United States Patent
Zhou et al.

(10) Patent No.: US 9,040,739 B2
(45) Date of Patent: May 26, 2015

(54) CATALYST AND METHOD FOR SYNTHESIS OF LACTIC ACID AND ITS DERIVATIVES

(75) Inventors: Xiaoping Zhou, Huzhou (CN); Rui Bi, Huzhou (CN)

(73) Assignee: MICROVAST POWER SYSTEMS CO., LTD., Huzhou, Zhejiang Province (CN)

( * ) Notice: Subject to any disclaimer, the term of this patent is extended or adjusted under 35 U.S.C. 154(b) by 297 days.

(21) Appl. No.: 13/596,043

(22) Filed: Aug. 27, 2012

(65) Prior Publication Data

US 2013/0338397 A1      Dec. 19, 2013

(30) Foreign Application Priority Data

Jun. 18, 2012   (CN) .......................... 2012 1 0204319

(51) Int. Cl.
| | |
|---|---|
| *C07C 69/68* | (2006.01) |
| *B01J 23/14* | (2006.01) |
| *B01J 27/135* | (2006.01) |
| *B01J 31/02* | (2006.01) |
| *B01J 31/26* | (2006.01) |
| *C07C 51/00* | (2006.01) |
| *C07C 59/08* | (2006.01) |
| *C07C 67/00* | (2006.01) |

(52) U.S. Cl.
CPC ................ *B01J 23/14* (2013.01); *B01J 27/135* (2013.01); *B01J 31/02* (2013.01); *B01J 31/26* (2013.01); *C07C 51/00* (2013.01); *C07C 59/08* (2013.01); *C07C 67/00* (2013.01)

(58) Field of Classification Search
CPC ........ C07C 51/00; C07C 59/08; C07C 69/68; C07C 67/00; B01J 23/14
See application file for complete search history.

(56) References Cited

U.S. PATENT DOCUMENTS

2013/0204036 A1 *   8/2013   Tominaga et al. ............ 560/179

FOREIGN PATENT DOCUMENTS

| | | | |
|---|---|---|---|
| GB | 467510 | * | 12/1935 |
| WO | WO 2011/125882 A1 | * | 10/2011 |

* cited by examiner

*Primary Examiner* — Paul A Zucker
(74) *Attorney, Agent, or Firm* — Cheng-Ju Chiang

(57) ABSTRACT

A catalyst for synthesis of lactic acid and it derivatives is provided. The catalyst includes $SnY_2 \cdot mH_2O$ and at least one of $NH_4X$ or quaternary ammonium salts, wherein X and Y are selected from F—, Cl—, Br—, I—, $CH_3SO_3$—, $C_6H_5SO_3$—, $CH_3C_6H_4SO_3$— or CN—, m represents an integer of 1 to 15. A method for synthesis of lactic acid and it derivatives with the above catalyst is also provided. By using the above catalyst and method, it is capable of converting carbohydrate-containing raw material to lactic acid and its derivatives directly in a more efficient and economical way.

19 Claims, 2 Drawing Sheets

CATALYST AND METHOD FOR SYNTHESIS OF LACTIC ACID AND ITS DERIVATIVES

FIELD OF THE INVENTION

This invention generally relates to synthesis of lactic acid and its derivatives, and more particularly to a catalyst and a method for synthesis of lactic acid and its derivatives.

BACKGROUND OF THE INVENTION

Glucose, sugarcane, starch, and celluloses are the most abundant renewable carbon sources found naturally on the earth. The high content of oxygenated functional groups in these carbohydrates has advantages in making use of them to produce fundamental chemicals. In particular, these carbohydrates are the most attractive feedstocks for intermediate chemical production in a sustainable way without emitting $CO_2$.

Theoretically, two moles of lactic acid could be obtained from one mole of hexose either by fermentation or by catalytic reaction. Lactic acid itself is a monomer for the biodegradable polylactate synthesis. Lactic acid and its derivatives (such as alkyl lactates and polylactate) could act as platform compounds for the synthesis of other carbon-3 building blocks, such as propylene glycol, acrylic acid, and allyl alcohol for the productions of polymers.

Lactic acid is produced by the fermentation of glucose in present chemical industry. FIG. 1 shows the scheme for lactic acid and its derivatives preparation according to a commercial fermentation process. In the fermentation process, the concentration of lactic acid in the obtained water solution is very low. For example, the weight ratio of the lactic acid may be less than 10%. In addition, to isolate the lactic acid from the water solution, $Ca(OH)_2$ should be added into the water solution, and $Ca(OH)_2$ reacts with lactic acid thereby producing calcium lactate solid. Then, the calcium lactate solid is separated and added into $H_2SO_4$ solution. Accordingly, lactic acid is obtained, and $CaSO_4$ solid precipitates in the lactic acid. Obviously, in the fermentation process described above, huge amounts of waste water and $CaSO_4$ solid waste was produced, and only glucose can be used as the feedstock. Lactic acid could be produced from glucose in large scale (120,000 tons/year) in the existing fermentation processes. However, the biological processes generally suffer from low reaction rates and low product concentration (in water), resulting in long reaction times, larger reactors, and high energy consumption in the product purification process (Fermentation of Glucose to Lactic Acid Coupled with Reactive Extraction: Kailas L. Wasewar, Archis A. Yawalkar, Jacob A. Moulijn and Vishwas G. Pangarkar, Ind. Eng. Chem. Res. 2004, 43, 5969-5982).

It is known that, in the presence of aqueous alkali hydroxides, monosaccharides can be converted to lactic acid (R. Montgomery, Ind. Eng. Chem., 1953, 45, 1144; B. Y. Yang and R. Montgomery, Carbohydr. Res. 1996, 280, 47). However, the stoichiometric amount of base ($Ca(OH)_2$) and acid ($H_2SO_4$) in the lactic acid recovery process would be consumed and, therefore, the stoichiometric amount of salt waste would be produced.

Although the commercial fermentation approach can produce large scale lactic acid, it only uses starch as a feedstock and the starch must be prehydrolyzed (or through fermentation) to glucose in advance. The fermentation process produces large amounts of waste water and solid waste ($CaSO_4$). And the fermentation process for producing lactic acid includes many steps, which consume substantial amounts of energy. The infrastructure of the fermentation process is very complicated and uneconomical.

SUMMARY OF THE INVENTION

It is desired to have a process to convert carbohydrate-containing raw material to lactic acid and its derivatives in a more efficient and economical way.

A catalyst for synthesis of lactic acid and it derivatives, includes $SnY_2 \cdot mH_2O$ and at least one of $NH_4X$ or quaternary ammonium salts, wherein X and Y are selected from F—, Cl—, Br—, I—, $CH_3SO_3$—, $C_6H_5SO_3$—, $CH_3C_6H_4SO_3$— or CN—, m represents an integer of 1 to 15.

A method for synthesis of lactic acid and its derivatives is also provided. First, a mixture is prepared, which includes: at least one carbohydrate-containing raw material, at least one alcohol, at least one catalyst, and at least one solvent, wherein the catalyst comprising $SnY_2 \cdot mH_2O$ and at least one of $NH_4X$ or quaternary ammonium salts, wherein X and Y are selected from F—, Cl—, Br—, I—, $CH_3SO_3$—, $C_6H_5SO_3$—, $CH_3C_6H_4SO_3$— or CN—, m represents an integer of 1 to 15. Then, the mixture is heated to obtain lactic acid and its derivatives.

By using the above described catalyst and method, it is capable of converting carbohydrate-containing raw material to lactic acid and its derivatives directly, and pure lactic acid and its derivatives can be obtained after a simple distillation process. Compared with conventional commercially employed fermentation process, the newly proposed process has the advantages of simplified steps and reactors, no need to use huge amounts of acid and base to purify the products, low energy consumption and no solid waste production.

DETAILED DESCRIPTION OF PREFERRED EMBODIMENTS

The detailed descriptions of the present invention set forth below in connection with the examples are preferred embodiments of the present invention, but the present invention is not limited to the embodiments and forms described hereinafter.

This disclosure provides a catalyst for synthesis of lactic acid and its derivatives. The catalyst includes $SnY_2 \cdot mH_2O$ and at least one of $NH_4X$ or quaternary ammonium salts, wherein X and Y are selected from $F^-$, $Cl^-$, $Br^-$, $I^-$, $CH_3SO_3^-$, $C_6H_5SO_3^-$, $CH_3C_6H_4SO_3^-$ or $CN^-$, m is the number of the crystallization water, which represents an integer of 1 to 15.

X and Y can further be selected from F—, Cl—, Br—, I—, or CN—.

The cation of the quaternary ammonium salts is an organic cation that has the general formula of $(NR_1R_2R_3R_4)^+$, in which, the $R_1$, $R_2$, $R_3$, and $R_4$ are alkyl groups with formula of $C_nH_{2n+1}$, wherein n represents an integer of 1 to 30.

In addition, a mass ratio of the at least one of $NH_4X$ or quaternary ammonium salts to the $SnY_2 \cdot mH_2O$ is in a range from 1:2 to 5:2. For example, the ratio may be 1:2, 70:33, 2:1 or 5:2. It is understood that these are only illustrative examples, but their disclosure is not intended to limit the values of the ratio.

By using the above described catalyst, it is capable of converting carbohydrate-containing raw material to lactic acid and its derivatives directly, and pure lactic acid and its derivatives can be obtained after a simple distillation process. Compared with conventional commercially employed fermentation process, the newly proposed process has the advantages of simplified steps and reactors, no need to use huge amounts of acid and base to purify the products, low energy consumption and no solid waste production.

Figure 1:
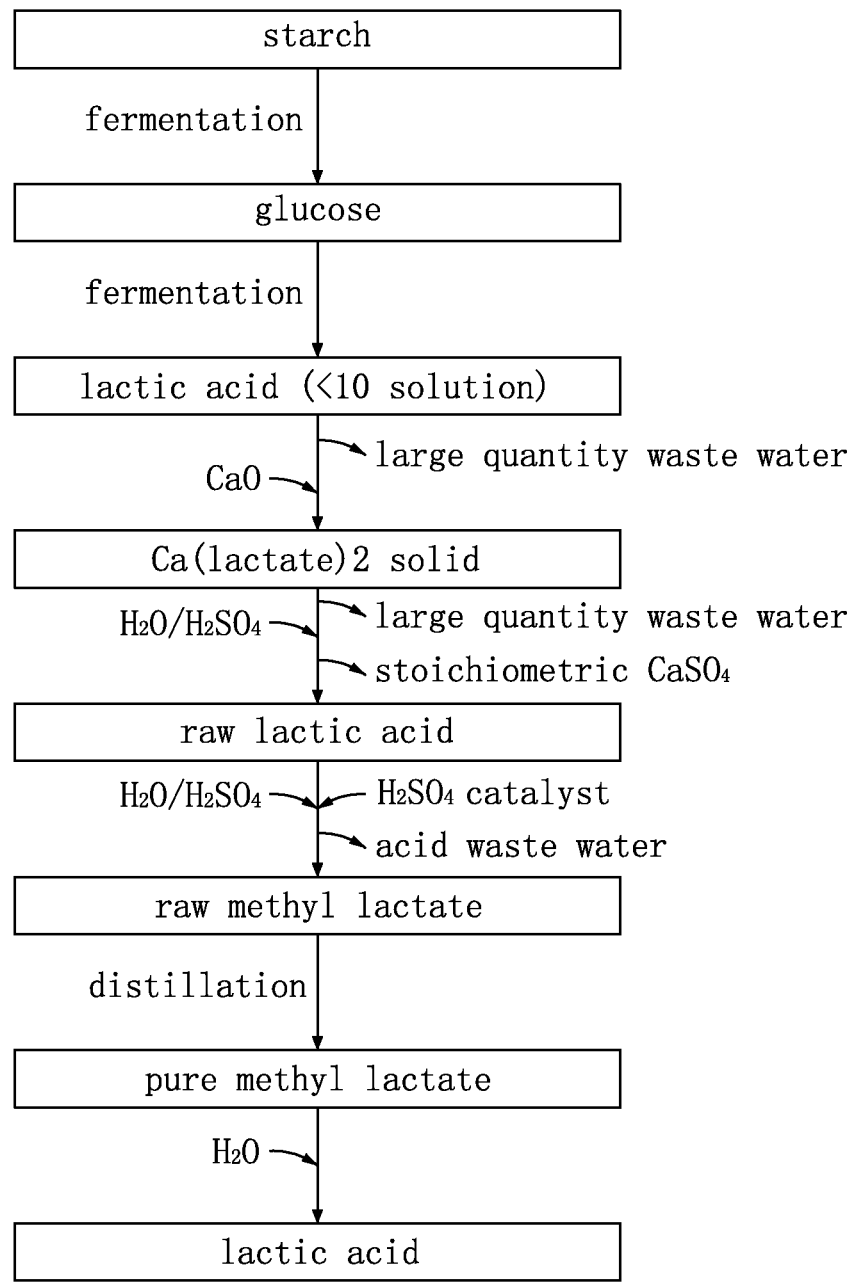
FIG. 1 shows the scheme fo r lactic acid preparation according to a commercial fermentation process.
Figure 2:
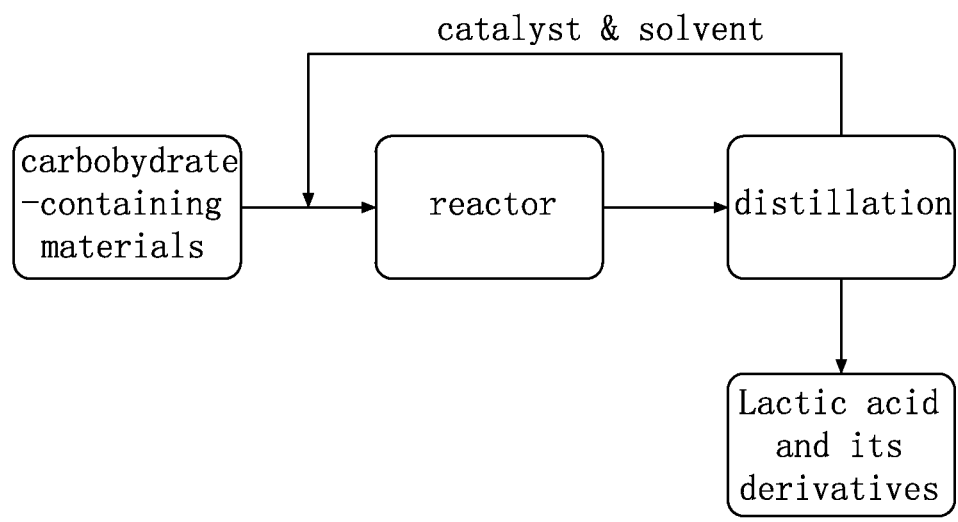
FIG. 2 shows the scheme of a method for synthesis of lactic acid and its derivatives in accordance with an embodiment of the present invention.

This disclosure further provides a method for synthesis of lactic acid and its derivatives. Referring to FIG. 2, in this method, carbohydrate-containing raw material, the above described catalyst, an alcohol and a solvent are added into a reactor, and then heated to carry out the reaction. The obtained solution is distilled to obtain lactic acid and its derivatives, and the catalyst can be reused.

The alcohol is selected from the group consisting of monohydric alcohols, dihydric alcohols, and trihydric alcohols. Further, the monohydric alcohol is selected from at least one of methanol, ethanol, 1-propanol, 2-propanol, 1-butanol, 2-butanol, and tert-butanol. The dihydric alcohol is selected from the group consisting of ethylene glycol, 1,2-propanediol, and 1,3-propanediol. The trihydric alcohol is glycerol.

A mass ratio of the alcohol to the carbohydrate-containing raw material is greater than 1, and in other embodiments, the mass ratio of the alcohol to the carbohydrate-containing raw material is further greater than 3:2.

The solvent, for example, is a polar solvent, such as water, alcohols, the methyl esters of C8 to C22 fatty acids, or mixtures thereof, which could dissolve the catalyst to form a homogeneous catalyst solution.

A reaction temperature of the heating step is between 25 and 200° C., and more preferably, the reaction temperature of the heating step is between 25 and 180° C.

In addition, the reaction temperature can be further adjusted according to different composition of the carbohydrate-containing raw material.

In a specific embodiment, the carbohydrate-containing raw material is cellulose and the reaction temperature is between 80 and 180° C.; more preferably, the reaction temperature is between 80 and 160° C.

In a specific embodiment, the carbohydrate-containing raw material is starch and the reaction temperature is between 80 and 180° C.; more preferably, the reaction temperature is between 80 and 160° C.

In a specific embodiment, the carbohydrate-containing raw material is sucrose or glucose and the reaction temperature is between 25 and 180° C.; more preferably, the reaction temperature is between 25 and 140° C.

By using the above described method, it is capable of converting carbohydrate-containing raw material to lactic acid and its derivatives directly, and pure lactic acid and its derivatives can be obtained after a simple distillation process. Compared with conventional commercially employed fermentation process, the newly proposed process has the advantages of simplified steps and reactors, no need to use huge amounts of acid and base to purify the products, low energy consumption and no solid waste production.

Example 1

Reaction Results of Sucrose

In the reaction, 0.200 g of $SnCl_2.2H_2O$ and 0.100 g of $NH_4Cl$ were added into a reactor (inside volume 12.0 mL) as catalyst. 6.0 mL of methanol, 0.200 g of water, and 0.200 g of sucrose were added into a reactor, and then the reactor was sealed and heated to 130° C. under stirring to carry out the reaction (from 25 to 130° C. within 25 min) The reaction was carried out at 130° C. for 2 h. The product was analyzed by gas chromatograph with thermal conductivity detector (GC-TCD). The yield of methyl lactate is 45%.

Example 2

Reaction Results of Sucrose

In the reaction, 0.200 g of $SnCl_2.2H_2O$ and 0.500 g of $NH_4Cl$ were added into a reactor (inside volume 12.0 mL) as catalyst. 6.0 mL of methanol, 0.200 g of water, and 1.00 g of sucrose were added into a reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is 33%.

Example 3

Reaction Results of Sucrose

In the reaction, 0.200 g of $SnCl_2.2H_2O$ and 0.500 g of $[N(CH_3)_3(n-C_{18}H_{37})]Cl$ were added into a reactor (inside volume 12.0 mL) as catalyst. 6.0 mL of methanol, 0.200 g of water, and 0.200 g of sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is 50%.

Example 4

Reaction Results of Sucrose

In the reaction, 0.200 g of $SnCl_2.2H_2O$ and 0.500 g of $[N(CH_3)_2(n-C_{18}H_{37})_2]Cl$ were added into a reactor (inside volume 12.0 mL) as catalyst. 6.0 mL of methanol, 0.200 g of water, and 0.200 g of sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is 43%.

Example 5

Reaction Results of Starch

In the reaction, 0.200 g of $SnCl_2.2H_2O$ and 0.500 g of $[N(CH_3)_3(n-C_{14}H_{29})]Cl$ were added into a reactor (inside volume 12.0 mL) as catalyst. 6.0 mL of methanol, 0.200 g of water, and 0.200 g of sucrose were added into the reactor, and then the reactor was sealed and heated to 160° C. under stirring to carry out the reaction (from 25 to 160° C. within 25 min) The reaction was carried out at 160° C. for 8 h. The product was analyzed by GC-TCD. The yield of methyl lactate is 35%.

Example 6

Reaction Results of Corn Sucrose

In the reaction, 0.200 g of $Sn(CH_3SO_3)_2$ and 0.500 g of $[N(CH_3)_3(n-C_{18}H_{37})]Cl$ were added into a reactor (inside volume 12.0 mL) as catalyst. 6.0 mL of methanol, 0.200 g of water, and 0.200 g of sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is 43%.

Example 7

Reaction Results of Sucrose

In the reaction, 100.0 g of $SnCl_2 \cdot 2H_2O$ and 200.0 g of $NH_4Cl$ were added into a reactor (inside volume 10.0 L) as catalyst, and then 3.750 L of methanol was added into the reactor. The reactor was sealed and heated to 130° C. under stirring. 800.0 g of water and 500.0 g of sucrose were mixed to obtain a solution, which was pumped into the reactor with a flow of 8.0 mL/min to carry out reaction. After pumping all of the sucrose aqueous solution, continue 1 more hour at 130° C. to complete the reaction. The product was analyzed by GC-TCD. The yield of methyl lactate is 37%.

Example 8

Reaction Results of Sucrose

In the reaction, 0.200 g of $SnCl_2 \cdot 2H_2O$ and 0.500 g of quaternary ammonium chloride were added into a reactor (inside volume 12.0 mL) as catalyst. 6.0 mL of methanol, 0.200 g of water, and 0.200 g of sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is given in Table 1.

TABLE 1

Reaction results of sucrose

| $H_2O$ (g) | $SnCl_2 \cdot 2H_2O$ (g) | 0.500 (g) | t (h) | T (° C.) | Y (%) |
|---|---|---|---|---|---|
| 0.200 | 0.200 | $[N(CH_3)_3(n\text{-}C_{18}H_{37})]Cl$ | 2 | 130 | 59 |
| 0.200 | 0.200 | $[N(CH_3)_3(n\text{-}C_{16}H_{33})]Cl$ | 2 | 130 | 49 |
| 0.200 | 0.200 | $[N(CH_3)_3(n\text{-}C_{14}H_{29})]Cl$ | 2 | 130 | 47 |
| 0.200 | 0.200 | $[N(CH_3)_3(n\text{-}C_{12}H_{25})]Cl$ | 2 | 130 | 42 |
| 0.200 | 0.200 | $[N(CH_3)_4]Cl$ | 2 | 130 | 30 |
| 0.200 | 0.200 | $N(C_8H_{17})_3$ | 2 | 130 | 10 |
| 0.200 | 0.200 | $[N(CH_3)_2(n\text{-}C_{18}H_{37})_2]Cl$ | 2 | 130 | 43 |
| 0.200 | 0.200 | $[N(CH_3)_2(n\text{-}C_{12}H_{25})_2]Cl$ | 2 | 130 | 35 |
| 0.200 | 0.200 | $[N(CH_3)_2(n\text{-}C_{10}H_{21})_2]Cl$ | 2 | 130 | 46 |

Example 9

Reaction Results of Starch

In the reaction, 0.200 g of $SnCl_2 \cdot 2H_2O$ and 0.500 g of quaternary ammonium chloride were added into a reactor (inside volume 12.0 mL) as catalyst. 6.0 mL of methanol, 0.200 g of water, and 0.200 g of starch were added into the reactor, and then the reactor was sealed and heated to 160° C. under stirring to carry out the reaction (from 25 to 160° C. within 25 min) The reaction was carried out at 160° C. for 8 h. The product was analyzed by GC-TCD. The yield of methyl lactate is given in Table 2.

TABLE 2

Reaction results of starch

| $H_2O$ (g) | $SnCl_2 \cdot 2H_2O$ (g) | 0.500 (g) | t (h) | T (° C.) | Y (%) |
|---|---|---|---|---|---|
| 0.200 | 0.200 | $[N(CH_3)_3(n\text{-}C_{18}H_{37})]Cl$ | 8 | 160 | 37 |
| 0.200 | 0.200 | $[N(CH_3)_3(n\text{-}C_{16}H_{33})]Cl$ | 8 | 160 | 34 |
| 0.200 | 0.200 | $[N(CH_3)_3(n\text{-}C_{14}H_{29})]Cl$ | 8 | 160 | 34 |
| 0.200 | 0.200 | $[N(CH_3)_3(n\text{-}C_{12}H_{25})]Cl$ | 8 | 160 | 35 |
| 0.200 | 0.200 | $[N(CH_3)_4]Cl$ | 8 | 160 | 36 |
| 0.200 | 0.200 | $N(C_8H_{17})_3$ | 8 | 160 | 2 |

Example 10

Reaction Results of Sucrose

In the reaction, 0.200 g of $SnCl_2 \cdot 2H_2O$ and 0.500 g of quaternary ammonium chloride were added into a reactor (inside volume 12.0 mL) as catalyst. 6.0 mL of methanol, 0.200 g of water, and sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is given in Table 3.

TABLE 3

Reaction results of starch

| sucrose (g) | $SnCl_2 \cdot 2H_2O$ (g) | $[N(CH_3)_3(n\text{-}C_{18}H_{37})]Cl$ | t (h) | T (° C.) | Y (%) |
|---|---|---|---|---|---|
| 0.200 | 0.200 | 0.500 (g) | 2 | 130 | 59 |
| 0.400 | 0.200 | 0.500 (g) | 2 | 130 | 45 |
| 0.600 | 0.200 | 0.500 (g) | 2 | 130 | 44 |
| 0.800 | 0.200 | 0.500 (g) | 2 | 130 | 43 |
| 1.000 | 0.200 | 0.500 (g) | 2 | 130 | 38 |
| 1.200 | 0.200 | 0.500 (g) | 2 | 130 | 37 |
| 2.000 | 0.200 | 0.500 (g) | 2 | 130 | 28 |

Example 11

Reaction Results of Sucrose

In the reaction, 0.200 g of $SnCl_2 \cdot 2H_2O$ and 0.500 g of quaternary ammonium chloride were added into a reactor (inside volume 12.0 mL) as catalyst. 6.0 mL of methanol, 0.200 g of water, and sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is given in Table 4.

TABLE 4

Reaction results of sucrose

| sucrose (g) | $SnCl_2 \cdot 2H_2O$ (g) | $[N(CH_3)_3(n\text{-}C_{16}H_{33})]Cl$ | t (h) | T (° C.) | Y (%) |
|---|---|---|---|---|---|
| 0.200 | 0.200 | 0.500 (g) | 2 | 130 | 49 |
| 0.400 | 0.200 | 0.500 (g) | 2 | 130 | 45 |
| 0.600 | 0.200 | 0.500 (g) | 2 | 130 | 42 |
| 0.800 | 0.200 | 0.500 (g) | 2 | 130 | 37 |
| 1.000 | 0.200 | 0.500 (g) | 2 | 130 | 37 |
| 1.200 | 0.200 | 0.500 (g) | 2 | 130 | 40 |
| 2.000 | 0.200 | 0.500 (g) | 2 | 130 | 35 |

Example 12

Reaction Results of Sucrose

In the reaction, 0.200 g of $Sn(CH_3SO_3)_2$ and 0.500 g of quaternary ammonium chloride were added into a reactor (inside volume 12.0 mL) as catalyst. 6.0 mL of methanol, 0.200 g of water, and 0.200 g of sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is given in Table 5.

TABLE 5

Reaction results of starch

| $H_2O$ (g) | $Sn(CH_3SO_3)_2$ (g) | 0.500 (g) | t (h) | T (° C.) | Y (%) |
|---|---|---|---|---|---|
| 0.200 | 0.200 | $[N(CH_3)_3(n\text{-}C_{18}H_{37})]Cl$ | 2 | 130 | 43.34 |
| 0.200 | 0.200 | $[N(CH_3)_3(n\text{-}C_{16}H_{33})]Cl$ | 2 | 130 | 39.84 |

Example 13

Reaction Results of Sucrose

In the reaction, 0.200 g of $SnCl_2.2H_2O$ and $NH_4Cl$ were added into a reactor (inside volume 12.0 mL) as catalyst. 6.0 mL of methanol, 0.200 g of water, and sucrose were added into the reactor, and then the reactor was sealed and heated to 130° C. under stirring to carry out the reaction (from 25 to 130° C. within 25 min) The reaction was carried out at 130° C. for 2 h. The product was analyzed by GC-TCD. The yield of methyl lactate is given in Table 6.

TABLE 6

Reaction results of sucrose

| sucrose (g) | $SnCl_2 \cdot 2H_2O$ (g) | $NH_4Cl$ (g) | t (h) | T (° C.) | Y (%) |
|---|---|---|---|---|---|
| 0.200 | 0.200 | 0.100 | 2 | 130 | 45.15 |
| 0.200 | 0.200 | 0.200 | 2 | 130 | 47.5 |
| 0.200 | 0.200 | 0.300 | 2 | 130 | 38.3 |
| 0.200 | 0.200 | 0.400 | 2 | 130 | 37.26 |
| 0.200 | 0.200 | 0.600 | 2 | 130 | 34.01 |
| 0.200 | 0.200 | 1.000 | 2 | 130 | 39.6 |
| 1.000 | 0.200 | 0.500 | 2 | 130 | 33.53 |
| 1.000 | 0.200 | 1.000 | 2 | 130 | 25.1 |
| 1.000 | 0.200 | 1.500 | 2 | 130 | 41.16 |
| 1.000 | 0.200 | 2.000 | 2 | 130 | 27.38 |
| 1.000 | 0.200 | 2.500 | 2 | 130 | 26.96 |

Example 14

Reaction Results in 10 Liter Reactor

In the reaction, 100 g of $SnCl_2.2H_2O$ and 200 g of $NH_4Cl$ were added into a reactor (inside volume 10.0 L) as catalyst. 3.0 kg of methanol was also added into the reactor. The reactor was sealed and heated to 130° C. under stirring. A solution of 0.500 kg sucrose in 0.800 kg water was pumped into the reactor with a flow of 10.0 mL/min to carry out the reaction. After pumping all of the sucrose solution into the reactor, the reaction was kept running for another 1.5 h to complete the reaction. The resulted solution was analyzed by GC and high-performance liquid chromatography (HPLC). 80.2% of total molar yield of methyl lactate and lactic acid was obtained. The reaction was reproduced and a total yield of methyl lactate and lactic acid of 95.0% was obtained.

Example 15

Reaction Results in 10 Liter Reactor

In the reaction, 50 g of $SnCl_2.2H_2O$ and 100 g of $NH_4Cl$ were added into a reactor (inside volume 10.0 L) as catalyst. 3.0 kg of methanol was also added into the reactor. The reactor was sealed and heated to 130° C. under stirring. A solution of 0.500 kg sucrose in 0.500 kg water was pumped into the reactor with a flow of 10.0 mL/min to carry out the reaction. After pumping all of the sucrose solution into the reactor, the reaction was kept running for another 1.5 h to complete the reaction. The resulted solution was analyzed by GC and HPLC. 80.7% of total molar yield of methyl lactate and lactic acid was obtained.

Example 16

Reaction Results in 10 Liter Reactor

In the reaction, 33 g of $SnCl_2.2H_2O$ and 70 g of $NH_4Cl$ were added into a reactor (inside volume 10.0 L) as catalyst. 3.0 kg of methanol was also added into the reactor. The reactor was sealed and heated to 130° C. under stirring. A solution of 0.500 kg sucrose in 0.500 kg water was pumped into the reactor with a flow of 10.0 mL/min to carry out the reaction. After pumping all of the sucrose solution into the reactor, the reaction was kept running for another 1.5 h to complete the reaction. The resulted solution was analyzed by GC and HPLC. 81% of total molar yield of methyl lactate and lactic acid was obtained.

Example 17

Reaction Results in 10 Liter Reactor

In the reaction, 20 g of $SnCl_2.2H_2O$ and 40 g of $NH_4Cl$ were added into a reactor (inside volume 10.0 L) as catalyst. 3.0 kg of methanol was also added into the reactor. The reactor was sealed and heated to 130° C. under stirring. A solution of 0.500 kg sucrose in 0.500 kg water was pumped into the reactor with a flow of 10.0 mL/min to carry out the reaction. After pumping all of the sucrose solution into the reactor, the reaction was kept running for another 1.5 h to complete the reaction. The resulted solution was analyzed by GC and HPLC. 71% of total molar yield of methyl lactate and lactic acid was obtained.

Example 18

Reaction Results in 10 Liter Reactor

In the reaction, 100 g of $SnCl_2.2H_2O$ and 200 g of $NH_4Cl$ were added into a reactor (inside volume 10.0 L) as catalyst. 3.0 kg of methanol was also added into the reactor. A mixture of 0.500 kg corn powder (containing 71% starch) in 0.500 kg water was added into the reactor and sealed the reactor to carry out reaction at 160° C. for 8 h. The resulted solution was analyzed by GC and HPLC. 54% of total molar yield of methyl lactate and lactic acid was obtained.

Example 19

Reaction Results in 10 Liter Reactor

In the reaction, 100 g of $SnCl_2 \cdot 2H_2O$ and 200 g of $NH_4Cl$ were added into the reactor (inside volume 10.0 L) as catalyst. 3.0 kg of methanol was also added into the reactor. The reactor was sealed and heated to 130° C. under stirring. A solution of 0.500 kg glucose in 0.500 kg water was pumped into the reactor with a flow of 10.0 mL/min to carry out the reaction. After pumping all of the glucose solution into the reactor, the reaction was kept running for another 1.5 h to complete the reaction. The resulted solution was analyzed by GC and HPLC. 64% of total molar yield of methyl lactate and lactic acid was obtained.

The above descriptions are only preferred embodiments of the present invention, and are not intended to limit the present invention. Any amendments, replacement and modification made to the above embodiments under the spirit and principle of the present invention should be included in the scope of the present invention.

What is claimed is:

1. A catalyst for synthesis of lactic acid and its derivatives, comprising:
    $SnY_2 \cdot mH_2O$ and at least one of $NH_4X$ or quaternary ammonium salts, wherein X and Y are selected from $F^-$, $Cl^-$, $Br^-$, $I^-$, $CH_3SO_3^-$, $C_6H_5SO_3^-$, $CH_3C_6H_4SO_3^-$ or $CN^-$, m represents an integer of 1 to 15, and the mass ratio of the at least one of $NH_4X$ or quaternary ammonium salts to the $SnY_2 \cdot mH_2O$ is in a range from 1:2 to 5:2.

2. The catalyst for synthesis of lactic acid and its derivatives of claim 1, wherein the cation of the quaternary ammonium salts has a general formula of $(NR_1R_2R_3R_4)^+$, in which, the $R_1$, $R_2$, $R_3$, and $R_4$ are alkyl groups with formula of $C_nH_{2n+1}$, wherein n represents an integer of 1 to 30.

3. A method for synthesis of lactic acid and its derivatives, comprising:
    providing a mixture, comprising: at least one carbohydrate-containing raw material, at least one alcohol, at least one catalyst, and at least one solvent, wherein the catalyst comprising $SnY_2 \cdot mH_2O$ and at least one of $NH_4X$ or quaternary ammonium salts, wherein X and Y are selected from $F^-$, $Cl^-$, $Br^-$, $I^-$, $CH_3SO_3^-$, $C_6H_5SO_3^-$ $CH_3C_6H_4SO_3^-$ or $CN^-$, m represents an integer of 1 to 15, and the mass ratio of the at least one of $NH_4X$ or quaternary ammonium salts to the $SnY_2 \cdot mH_2O$ is in a range from 1:2 to 5:2; and
    heating the mixture to obtain lactic acid and its derivatives.

4. The method for synthesis of lactic acid and its derivatives of claim 3, wherein the alcohol is selected from the group consisting of monohydroxyl alcohols, dihydroxyl alcohols, and trihydroxyl alcohols.

5. The method for synthesis of lactic acid and its derivatives of claim 4, wherein the alcohol is a monohydroxyl alcohol, and the monohydroxyl alcohol is selected from a group consisting of methanol, ethanol, 1-propanol, 2-propanol, 1-butanol, 2-butanol, and tert-butanol.

6. The method for synthesis of lactic acid and its derivatives of claim 4, wherein the alcohol is a dihydroxyl alcohol, and the dihydroxyl alcohol is selected from the group consisting of ethylene glycol, 1, 2-propandiol, and 1, 3-propandiol.

7. The method for synthesis of lactic acid and its derivatives of claim 4, wherein the alcohol is trihydroxyl alcohol, and the trihydroxyl alcohol is glycerol.

8. The method for synthesis of lactic acid and its derivatives of claim 3, wherein the mass ratio of the at least one alcohol to the at least one carbohydrate-containing raw material is greater than 1.

9. The method for synthesis of lactic acid and its derivatives of claim 8, wherein the mass ratio of the at least one alcohol to the at least one carbohydrate-containing raw material is greater than 3:2.

10. The method for synthesis of lactic acid and its derivatives of claim 3, wherein the at least one solvent is a polar solvent.

11. The method for synthesis of lactic acid and its derivatives of claim 10, wherein the polar solvent is selected from a group consisting of water, alcohols, the methyl esters of C8 to C22 fatty acids, or mixtures thereof.

12. The method for synthesis of lactic acid and its derivatives of claim 3, wherein a reaction temperature of the heating step is between 25 and 200° C.

13. The method for synthesis of lactic acid and its derivatives of claim 12, wherein the reaction temperature of the heating step is between 25 and 180° C.

14. The method for synthesis of lactic acid and its derivatives of claim 3, wherein the at least one carbohydrate-containing raw material comprises cellulose and the reaction temperature of the heating step is between 80 and 180° C.

15. The method for synthesis of lactic acid and its derivatives of claim 14, wherein the reaction temperature of the heating step is between 100 and 180° C.

16. The method for synthesis of lactic acid and its derivatives of claim 3, wherein the at least one carbohydrate-containing raw material comprises starch and the reaction temperature of the heating step is between 80 and 180° C.

17. The method for synthesis of lactic acid and its derivatives of claim 14, wherein the reaction temperature of the heating step is between 80 and 160° C.

18. The method for synthesis of lactic acid and its derivatives of claim 3, wherein the at least one carbohydrate-containing raw material comprises sucrose or glucose and the reaction temperature of the heating step is between 25 and 180° C.

19. The method for synthesis of lactic acid and its derivatives of claim 18, wherein the reaction temperature of the heating step is between 25 and 140° C.

* * * * *